United States Patent [19]
Targan et al.

[11] Patent Number: 5,874,233
[45] Date of Patent: Feb. 23, 1999

[54] METHODS OF DIAGNOSING A CLINICAL SUBTYPE OF CROHN'S DISEASE WITH FEATURES OF ULCERATIVE COLITIS

[75] Inventors: Stephan R. Targan, Los Angeles; Eric A. Vasiliauskas, Hermosa Beach; Scott E. Plevy, Pacific Palisades, all of Calif.

[73] Assignee: Cedars-Sinai Medical Center, Los Angeles, Calif.

[21] Appl. No.: 689,870

[22] Filed: Aug. 15, 1996

Related U.S. Application Data

[63] Continuation-in-part of Ser. No. 630,672, Apr. 12, 1996.
[51] Int. Cl.$^6$ .................... G01N 33/543; G01N 33/564
[52] U.S. Cl. .................... 435/7.24; 435/7.95; 436/506; 436/518
[58] Field of Search ................ 435/7.24, 7.95; 436/506, 518

[56] References Cited

FOREIGN PATENT DOCUMENTS

WO 95/21941  8/1995  WIPO.

OTHER PUBLICATIONS

Broekroelofs et al.,"Anti–Neutrophil Cytoplasmic Antibodies (ANCA) in Sera from Patients with Inflammatory Bowel Disease (IBD)," *Dig. Dis. Sci.* 39:545–549 (1994).
Cambridge et al., "Anti–neutrophil Antibodies in Inflammatory Bowel Disease: Prevalence and Diagnostic Role," *Gut* 33:668–674 (1992).
Duerr et al., "Anti–neutrophil Cytoplasmic Antibodies in Ulcerative Colitis," *Gastroenterol.*, 100:1590–1596 (1991).
Hardarson et al., "Antineutrophil Cytoplasmic Antibody in Inflammatory Bowel and Hepatobiliary Diseases," *Amer. J. Clin. Pathol.* 99:277–281 (1993).
Lennard–Jones, "Classification of Inflammatory Bowel Disease," *Scand. J. Gastroenterol. Suppl.* 24:2–6, 16–19 (1989).
Orholm et al., "Familial Occurrence of Inflammatory Bowel Disease," *N. Engl. J. Med.*, 324:84–88 (1991).
Patel et al., "Influence of Total Colectomy on Serum Antineutrophil Cytoplasmic Antibodies in Inflammatory Bowel Disease," *Brit. J. Surg.* 81:724–726 (1994).
Plevy et al., "Tumor Necrosis Factor Microsatellites Define a Crohn's Disease–Associated Haplotype on Chromosome 6," *Gastroenterology* 110:1053–1060 (1996).
Pool et al., "Serum Antineutrophil Cytoplasmic Autoantibodies in Inflammatory Bowel Disease are Mainly Associated with Ulcerative Colitis. A Correlation Study Between Between Perinuclear Antineutrophil Cytoplasmic Autoantibodies and Clinical Parameters, Medical, and Surgical Treatment," *Gut* 34:46–50 (1993).
Price, "Overlap in the Spectrum of Non–Specific Inflammatory Bowel Disease–'Colitis Indeterminate,'" *J. Clin. Pathol.* 31:567–577 (1978).
Proujansky et al., "Examination of Anti–neutrophil Cytoplasmic Antibodies in Childhood Inflammatory Bowel Disease," *J. Pediatr. Gastroenterol. Nutr.* 17:193–197 (1993).
Rubin and Farber (eds.), "Inflammatory Bowel Disease," *Pathology* (2nd Ed.), pp. 675–683 (1994).
Saxon et al., "A Distinct Subset of Antineutrophil Cytoplasmic Antibodies is Associated with Inflammatory Bowel Disease," *J. Allergy Clin. Immunol.* 86:202–210 (1990).
Schachter and Kirsner, "Definitions of Inflammatory Bowel Disease of Unknown Etiology," *Gastroenterol.* 68:591–600 (1975).
Sung et al., "Anti–Neutrophil Cytoplasmic Antibodies (ANCA) and Inflammatory Bowel Diseases in Chinese," *Dig. Dis. Sci.* 39:886–892 (1994).
Targan and Murphy, "Clarifying the Causes of Crohn's," *Nature Med.* 1:1241–1243 (1995).
Vasiliauskas et al., "Perinuclear Antineutrophil Cytoplasmic Antibodies (pANCA) in Patients with Crohn's Disease (CD) Define a Clinical Subgroup," *Gastroenterol.* 108:A935 (1995).
Vasiliauskas et al., "Perinucear Antineutrophil Cytoplasmic Antibodies in Patients with Crohn's Disease Define A Clinical Subgroup," *Gastroenterol.* 110:1810–19 (1996).
Yang et al., "Association of Intercellular Adhesion Molecule–1 (ICAM–1) Gene with Subsets of Inflammatory Bowel Disease (IBD) Stratified by Anti Neutrophil Cytoplasmic Antibodies (ANCAs)," *Clin. Res.* 42:76A (1994).
Yang et al., "Genetic Heterogeneity with UC and Crohn's Defined by Antineutrophil Cytoplasmic Antibodies (ANCAs) and Intercellular Adhesion Molecule–1 (ICAM–1) Polymorphisms," *Gastroenterol.* 106:A794 (1994).

*Primary Examiner*—David Saunders
*Attorney, Agent, or Firm*—Campbell & Flores LLP

[57] ABSTRACT

The present invention provides a method of diagnosing a clinical subtype of Crohn's disease (CD) by determining whether perinuclear anti-neutrophil antibodies (pANCA) are present in a patient with CD, where the presence of pANCA indicates the clinical subtype of CD with features of ulcerative colitis (UC). The invention also provides a method of diagnosing a clinical subtype of CD by detecting an $\text{Arg}^{241}$ allele at an ICAM-1 locus in a patient with CD, where the $\text{Arg}^{241}$ allele indicates a clinical subtype of CD with features of ulcerative colitis. In addition, the invention provides a method of diagnosing a pANCA-positive subtype of CD by detecting an $\text{Arg}^{241}$ allele at an ICAM-1 locus in a patient with CD, where the $\text{Arg}^{241}$ allele indicates the pANCA-positive subtype of CD.

8 Claims, 7 Drawing Sheets

ICAM

```
ATG GCT CCC AGC AGC CCC CGG CCC GCG CTG CCC GCA CTC CTG GTC CTG         48
Met Ala Pro Ser Ser Pro Arg Pro Ala Leu Pro Ala Leu Leu Val Leu
 1                   5                  10                  15

CTC GGG GCT CTG TTC CCA GGA CCT GGC AAT GCC CAG ACA TCT GTG TCC         96
Leu Gly Ala Leu Phe Pro Gly Pro Gly Asn Ala Gln Thr Ser Val Ser
            20                  25                  30

CCC TCA AAA GTC ATC CTG CCC CGG GGA GGC TCC GTG CTG GTG ACA TGC        144
Pro Ser Lys Val Ile Leu Pro Arg Gly Gly Ser Val Leu Val Thr Cys
        35                  40                  45

AGC ACC TCC TGT GAC CAG CCC AAG TTG TTG GGC ATA GAG ACC CCG TTG        192
Ser Thr Ser Cys Asp Gln Pro Lys Leu Leu Gly Ile Glu Thr Pro Leu
    50                  55                  60

CCT AAA AAG GAG TTG CTC CTG CCT GGG AAC AAC CGG AAG GTG TAT GAA        240
Pro Lys Lys Glu Leu Leu Leu Pro Gly Asn Asn Arg Lys Val Tyr Glu
65                  70                  75                  80

CTG AGC AAT GTG CAA GAT AGC CAA CCA ATG TGC TAT TCA AAC TGC            288
Leu Ser Asn Val Gln Asp Ser Gln Pro Met Cys Tyr Ser Asn Cys
                85                  90                  95

CCT GAT GGG CAG TCA ACA GCT AAA ACC TTC CTC ACC GTG TAC TGG ACT        336
Pro Asp Gly Gln Ser Thr Ala Lys Thr Phe Leu Thr Val Tyr Trp Thr
            100                 105                 110

CCA GAA CGG GAA GTG GAA CTG GCA CCC CTC CCC TCT TGG CAG CCA GTG GGC    384
Pro Glu Arg Glu Val Glu Leu Ala Pro Leu Pro Ser Trp Gln Pro Val Gly
        115                 120                 125
```

FIG. 4A

```
AAG AAC CTT ACC CTA CGC TGC CAG GTG GAG GGT GGG GCA CCC CGG GCC    432
Lys Asn Leu Thr Leu Arg Cys Gln Val Glu Gly Gly Ala Pro Arg Ala
130                 135                 140

AAC CTC ACC GTG GTG CTC CGT GGG GAG AAG GAG CTG AAA CGG GAG        480
Asn Leu Thr Val Val Leu Arg Gly Glu Lys Glu Leu Lys Arg Glu
145                 150                 155                 160

CCA GCT GTG GGG GAG CCC GCT GAG GTC ACG ACC ACG GTG CTG AGG        528
Pro Ala Val Gly Glu Pro Ala Glu Val Thr Thr Thr Val Leu Arg
        165                 170                 175

AGA GAT CAC CAT GGA GCC AAT TTC TCG TGC CGC ACT GAA CTG GAC CTG    576
Arg Asp His His Gly Ala Asn Phe Ser Cys Arg Thr Glu Leu Asp Leu
        180                 185                 190

CGG CCC CAA GGG CTG GAG CTG TTT GAG AAC ACC TCG GCC CCC TAC CAG    624
Arg Pro Gln Gly Leu Glu Leu Phe Glu Asn Thr Ser Ala Pro Tyr Gln
        195                 200                 205

CTC CAG ACC TTT GTC CTG CCA GCG ACG CCC CCA CAA CTT GTC AGC CCC    672
Leu Gln Thr Phe Val Leu Pro Ala Thr Pro Pro Gln Leu Val Ser Pro
210                 215                 220

CGG GTC CTA GAG GTG GAC ACG CAG GGG ACC GTG GTC TGT TCC CTG GAC    720
Arg Val Leu Glu Val Asp Thr Gln Gly Thr Val Val Cys Ser Leu Asp
225                 230                 235                 240

GGG CTG TTC CCA GTC TCG GAG GCC CAG GTC CAC CTG GCA CTG GGG GAC    768
Gly Leu Phe Pro Val Ser Glu Ala Gln Val His Leu Ala Leu Gly Asp
        245                 250                 255
```

FIG. 4B

```
CAG AGG TTG AAC CCC ACA GTC ACC TAT GGC AAC GAC TCC TTC TCG GCC      816
Gln Arg Leu Asn Pro Thr Val Thr Tyr Gly Asn Asp Ser Phe Ser Ala
            260                 265                 270

AAG GCC TCA GTC AGT GTG ACC GCA GAG GAC GAG GGC ACC CAG CGG CTG      864
Lys Ala Ser Val Ser Val Thr Ala Glu Asp Glu Gly Thr Gln Arg Leu
        275                 280                 285

ACG TGT GCA GTA ATA CTG GGG AAC CAG AGC CAG GAG ACA CTG CAG ACA      912
Thr Cys Ala Val Ile Leu Gly Asn Gln Ser Gln Glu Thr Leu Gln Thr
    290                 295                 300

GTG ACC ATC TAC AGC TTT CCG GCG CCC AAC GTG ATT CTG ACG AAG CCA      960
Val Thr Ile Tyr Ser Phe Pro Ala Pro Asn Val Ile Leu Thr Lys Pro
305                 310                 315                 320

GAG GTC TCA GAA GGG ACC GAG GTG ACA GTG AAG TGT GAG GCC CAC CCT     1008
Glu Val Ser Glu Gly Thr Glu Val Thr Val Lys Cys Glu Ala His Pro
                325                 330                 335

AGA GCC AAG GTG ACG CTG AAT GGG GTT CCA GCC CAG CCA CTG GGC CCG     1056
Arg Ala Lys Val Thr Leu Asn Gly Val Pro Ala Gln Pro Leu Gly Pro
            340                 345                 350

AGG GCC CAG CTC CTG CTG AAG GCC ACC CCA GAG GAC AAC GGG CGC AGC     1104
Arg Ala Gln Leu Leu Leu Lys Ala Thr Pro Glu Asp Asn Gly Arg Ser
        355                 360                 365

TTC TCC TGC TCT GCA ACC CTG GAG GTG GCC GGC CAG CTT ATA CAC AAG     1152
Phe Ser Cys Ser Ala Thr Leu Glu Val Ala Gly Gln Leu Ile His Lys
    370                 375                 380

AAC CAG ACC CGG GAG CTT CGT GTC CTG TAT GGC CCC CGA CTG GAC GAG     1200
Asn Gln Thr Arg Glu Leu Arg Val Leu Tyr Gly Pro Arg Leu Asp Glu
385                 390                 395                 400
```

FIG. 4C

```
AGG GAT TGT CCG GGA AAC TGG ACG TGG CCA GAA AAT TCC CAG CAG ACT      1248
Arg Asp Cys Pro Gly Asn Trp Thr Trp Pro Glu Asn Ser Gln Gln Thr
            405                     410                 415

CCA ATG TGC CAG GCT TGG GGG AAC CCA TTG CCC GAG CTC AAG TGT CTA      1296
Pro Met Cys Gln Ala Trp Gly Asn Pro Leu Pro Glu Leu Lys Cys Leu
            420                     425                 430

AAG GAT GGC ACT TTC CCA CTG CCC ATC GGG GAA TCA GTG ACT GTC ACT      1344
Lys Asp Gly Thr Phe Pro Leu Pro Ile Gly Glu Ser Val Thr Val Thr
            435                     440                 445

CGA GAT CTT GAG GGC ACC TAC CTC TGT CGG GCC AGG AGC ACT CAA GGG      1392
Arg Asp Leu Glu Gly Thr Tyr Leu Cys Arg Ala Arg Ser Thr Gln Gly
            450                     455                 460

GAG ACC CGC GAG ACT GTG AAT GTG GTA GCA GCC GCA GTC CTC TCC CCC CGG TAT GAG      1440
Glu Thr Arg Glu Thr Val Asn Val Ala Ala Ala Val Leu Ser Pro Arg Tyr Glu
            465                     470                 475                 480

ATT GTC ATC ATT ACT GTG GTA GCA GCC GCA GTC ATA ATG GGC ACT GCA      1488
Ile Val Ile Ile Thr Val Val Ala Ala Ala Val Ile Met Gly Thr Ala
            485                     490                 495

GGC CTC AGC ACG TAC CTC TAT AAC CGC CAG CAG AAG ATC AAG AAA TAC      1536
Gly Leu Ser Thr Tyr Leu Tyr Asn Arg Gln Arg Lys Ile Lys Lys Tyr
            500                     505                 510

AGA CTA CAA CAG GCC CAA AAA GGG ACC CCC ATG AAA CCG AAC ACA CAA      1584
Arg Leu Gln Gln Ala Gln Lys Gly Thr Pro Met Lys Pro Asn Thr Gln
            515                     520                 525

GCC ACG CCT CCC T GA                                                  1599
Ala Thr Pro Pro
    530
```

FIG. 4D

METHODS OF DIAGNOSING A CLINICAL SUBTYPE OF CROHN'S DISEASE WITH FEATURES OF ULCERATIVE COLITIS

This application is a continuation-in-part of U.S. Ser. No. 08/630,672, filed Apr. 12, 1996.

This work was supported by USPHS grant DK46763 awarded by The United States Public Health Service. The United States government has certain rights in this invention.

BACKGROUND OF THE INVENTION

1. Field of the Invention

The invention relates generally to the fields of autoimmunity and inflammatory bowel disease and more specifically to serological and genetic methods for diagnosing a clinical subtype of Crohn's disease.

2. Background Information

Inflammatory bowel disease (IBD) is the collective term used to describe two gastrointestinal disorders of unknown etiology: Crohn's disease (CD) and ulcerative colitis (UC). The course and prognosis of IBD, which occurs world-wide and is reported to afflict as many as two million people, varies widely. Onset of IBD is predominantly in young adulthood with diarrhea, abdominal pain, and fever the three most common presenting symptoms. The diarrhea may range from mild to severe and in ulcerative colitis often is accompanied by bleeding. Anemia and weight loss are additional common signs of IBD. Ten percent to fifteen percent of all patients with IBD will require surgery over a ten year period. In addition, patients with IBD are at increased risk for the development of intestinal cancer. Reports of an increasing occurrence of psychological problems, including anxiety and depression, are perhaps not surprising symptoms of what is often a debilitating disease that strikes people in the prime of life.

Progress has been made in diagnosing IBD and in distinguishing, in many cases, Crohn's disease from ulcerative colitis. However, CD and UC each can represent a number of distinct disease subtypes that affect the gastrointestinal tract and produce similar symptoms. The heterogeneity underlying CD, for example, can be reflected in the variable responses of CD patients to a particular treatment strategy. The availability of methods of diagnosing a clinical subtype of CD would represent a major clinical advance that would aid in the therapeutic management of CD and would provide a basis for the design of treatment modalities that are specific to a particular disease subtype. Unfortunately, a method of stratifying CD into clinical subtypes to allow the design of more precise treatment strategies is currently not available. Thus, there is a need for a method of diagnosing a clinical subtype of CD. The present invention satisfies this need and provides related advantages as well.

SUMMARY OF THE INVENTION

The present invention provides a method of diagnosing a clinical subtype of Crohn's disease (CD) by determining whether perinuclear anti-neutrophil antibody (pANCA) is present in a patient with CD, where the presence of pANCA indicates a clinical subtype of CD with features of ulcerative colitis (UC). Such a clinical subtype can be diagnosed, for example, by obtaining a serum sample from a patient with CD; determining whether anti-neutrophil cytoplasmic antibody (ANCA) is detectable in patient sera diluted at least about 100-fold; and assaying for the presence or absence of a pANCA staining pattern, where detection of ANCA in patient sera diluted at least about 100-fold and the presence of a pANCA staining pattern indicate the presence of pANCA, provided that detection of ANCA is not by histological methods.

The invention further provides a method of diagnosing a clinical subtype of CD by detecting an $Arg^{241}$ allele at an ICAM-1 locus in a patient with CD, where the $Arg^{241}$ allele indicates a clinical subtype of CD with features of ulcerative colitis. According to the methods of the invention, an $Arg^{241}$ allele can be detected by obtaining material from the patient with CD; preparing a nucleic acid comprising nucleotide 721 of SEQ ID NO: 1 from the material; contacting the nucleic acid with an $Arg^{241}$ allele-specific oligonucleotide probe under conditions suitable for formation of a specific hybrid between the nucleic acid and the $Arg^{241}$ allele-specific oligonucleotide probe; and assaying for the presence of the specific hybrid, where the presence of the specific hybrid indicates the $Arg^{241}$ allele.

In addition, the invention provides a method of diagnosing a pANCA-positive subtype of CD by detecting an $Arg^{241}$ allele at an ICAM-1 locus in a patient with CD, where the $Arg^{241}$ allele indicates the pANCA-positive subtype of CD. A pANCA-positive subtype of CD can be diagnosed according to the methods of the invention by obtaining material from a patient with CD; preparing a nucleic acid comprising nucleotide 721 of SEQ ID NO: 1 from the material; contacting the nucleic acid with an $Arg^{241}$ allele-specific oligonucleotide probe under conditions suitable for formation of a specific hybrid between the nucleic acid and the $Arg^{241}$ allele-specific oligonucleotide probe; and assaying for the presence of the specific hybrid, where the presence of the specific hybrid indicates the $Arg^{241}$ allele.

BRIEF DESCRIPTION OF THE DRAWINGS

FIGS. 4A–4D show the nucleic acid sequence (SEQ ID NO: 1) and corresponding amino acid sequence (SEQ ID NO: 12) of human intracellular adhesion molecule-1 (ICAM-1).

DETAILED DESCRIPTION OF THE INVENTION

Figure 1:
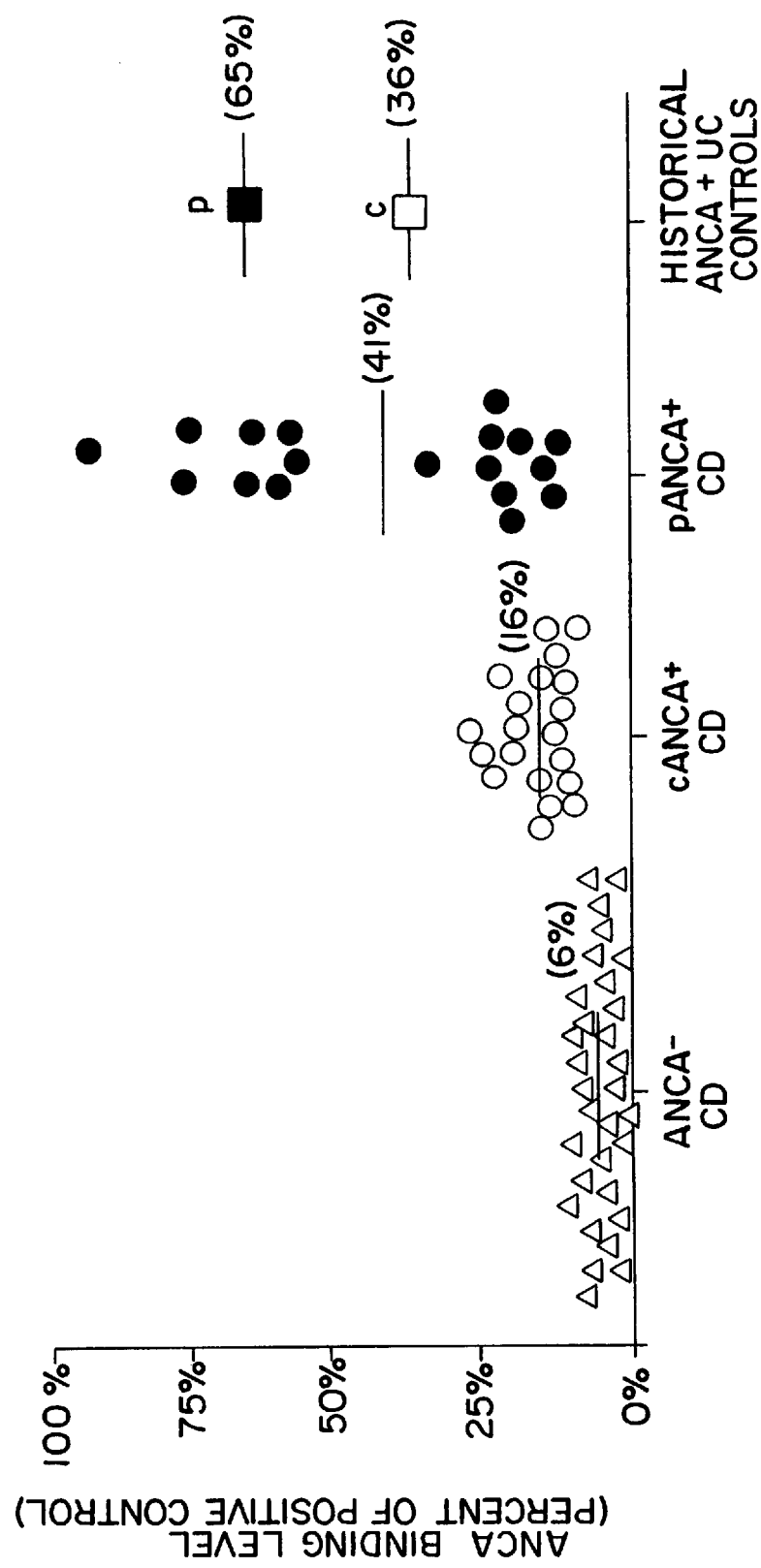
FIG. 1 shows the inflammatory disease-associated ANCA in sera from Crohn's disease patients analyzed by indirect immunofluorescence and by ELISA, with results expressed as percent of positive control. The solid line in each column represents the mean binding. respectively.

Although Crohn's disease (CD) and ulcerative colitis (UC) generally have been considered distinct diseases, the present invention is directed to the surprising discovery that there is a clinical subtype of CD patients that also have features of UC. The invention provides convenient, non-invasive serological and genetic assays for diagnosing this clinical subtype.

The invention provides a method of diagnosing a clinical subtype of Crohn's disease (CD) by determining whether pANCA is present in a patient with CD, where the presence of pANCA indicates a clinical subtype of CD with features of ulcerative colitis (UC). A method of the invention for diagnosing a clinical subtype of CD by determining whether pANCA is present in a patient with CD can be practiced by obtaining a serum sample from the patient with CD; determining whether anti-neutrophil cytoplasmic antibody (ANCA) is detectable in patient sera diluted at least about 100-fold; and assaying for the presence or absence of a pANCA staining pattern, where detection of ANCA in patient sera diluted at least about 100-fold and the presence of a pANCA staining pattern indicate the presence of pANCA, if the detection of ANCA is not by histological means.

As disclosed herein, the presence of pANCA in a Crohn's disease patient indicates a clinical subtype of CD, which is characterized by features of ulcerative colitis in addition to the features that are typical of CD. As described in Example IA, the presence of pANCA was determined in a group of 69 CD patients, where pANCA was determined to be present if ANCA was detectable in patient sera diluted 100-fold using a fixed neutrophil enzyme-linked immunosorbent assay (ELISA) and if a pANCA staining pattern was present as determined by indirect immunofluorescence using fixed neutrophil. Using these criteria to establish whether pANCA was present in a patient with CD, 100% percent of CD patients in which pANCA was present exhibited features of ulcerative colitis (see Example IB). The frequency of features of ulcerative colitis in the pANCA-positive CD subgroup was significantly higher than the frequency of features of ulcerative colitis in the cANCA-positive subgroup (45%) or the ANCA-negative CD subgroup (39%). Although Crohn's disease and ulcerative colitis generally have been considered to be distinct disorders, these results demonstrate that a subtype of patients have inflammatory bowel disease characterized by features of both UC and CD. The present invention provides a non-invasive assay based on the presence of pANCA to diagnose this clinical subtype of CD with features of ulcerative colitis.

The methods of the invention for diagnosing a clinical subtype of CD with features of ulcerative colitis are useful for the medical management of this subtype of Crohn's patients. The heterogeneity underlying Crohn's disease generally is reflected in variable responses of CD patients to a given treatment strategy. However, pANCA-positive CD patients suffer from a similar type of mucosal inflammation and respond similarly to a particular course of therapy. Furthermore, therapeutic strategies that are efficacious in the management of UC also can be used to treat the clinical subtype of CD with features of UC, while other Crohn's disease patients are unresponsive. For example, colectomy to remove diseased colonic mucosa with creation of an ileal pouch to preserve continence is frequently recommended for uncontrolled UC. While the general population of Crohn's disease patients typically cannot tolerate a pouch, such surgery can be a viable option for the subtype of CD patients whose disease is characterized by features of UC. Other therapeutic strategies, such as anti-tumor necrosis factor-α (TNF-α) inflammatories, for example, can best be used to treat Crohn's disease patients that are not pANCA-positive. Thus, the methods of the invention are useful for the differential diagnosis, treatment and medical management of patients having CD.

Inflammatory bowel disease has been classified into the broad categories of Crohn's disease and ulcerative colitis. Crohn's disease (regional enteritis) is a disease of chronic inflammation that can involve any part of the gastrointestinal tract. Commonly the distal portion of the small intestine (ileum) and cecum are affected. In other cases, the disease is confined to the small intestine, colon or anorectal region. Crohn's disease occasionally involves the duodenum and stomach, and more rarely the esophagus and oral cavity.

The variable clinical manifestations of Crohn's disease are, in part, a result of the varying anatomic localization of the disease. The most frequent symptoms of CD are abdominal pain, diarrhea and recurrent fever. CD is commonly associated with intestinal obstruction or fistula, which is an abnormal passage between diseased loops of bowel, for example. Crohn's disease also includes complications such as inflammation of the eye, joints and skin; liver disease; kidney stones or amyloidosis. In addition, CD is associated with an increased risk of intestinal cancer.

Several features are characteristic of the pathology of Crohn's disease. The inflammation associated with CD, known as transmural inflammation, involves all layers of the bowel wall. Thickening and edema, for example, typically also appear throughout the bowel wall, with fibrosis also present in long-standing disease. The inflammation characteristic of CD also is discontinuous in that segments of inflamed tissue, known as "skip lesions," are separated by apparently normal intestine. Furthermore, linear ulcerations, edema, and inflammation of the intervening tissue lead to a "cobblestone" appearance of the intestinal mucosa, which is distinctive of CD.

A hallmark of Crohn's disease is the presence of discrete aggregations of inflammatory cells, known as granulomas, which are generally found in the submucosa. About half of Crohn's disease cases display the typical discrete granulomas, while others show a diffuse granulomatous reaction or nonspecific transmural inflammation. As a result, the presence of discrete granulomas is indicative of CD, although the absence granulomas also is consistent with the disease. Thus, transmural or discontinuous inflammation, rather than the presence of granulomas, is a preferred diagnostic indicator of Crohn's disease (Rubin and Farber, *Pathology* (Second Edition) Philadelphia: J.B. Lippincott Company (1994), which is incorporated herein by reference).

Ulcerative colitis (UC) is a disease of the large intestine characterized by chronic diarrhea with cramping abdominal pain, rectal bleeding, and loose discharges of blood, pus and mucus. The manifestations of ulcerative colitis vary widely. A pattern of exacerbations and remissions typifies the clinical course of most UC patients (70%), although continuous symptoms without remission are present in some patients with UC. Local and systemic complications of UC include arthritis, eye inflammation such as uveitis, skin ulcers and liver disease. In addition, ulcerative colitis and especially long-standing, extensive disease is associated with an increased risk of colon carcinoma.

Several pathologic features characterize UC in distinction to other inflammatory bowel diseases. Ulcerative colitis is a diffuse disease that usually extends from the most distal part of the rectum for a variable distance proximally. The term left-sided colitis describes an inflammation that involves the distal portion of the colon, extending as far as the splenic flexure. Sparing of the rectum or involvement of the right side (proximal portion) of the colon alone is unusual in ulcerative colitis. The inflammatory process of ulcerative colitis is limited to the colon and does not involve, for example, the small intestine, stomach or esophagus. In addition, ulcerative colitis is distinguished by a superficial inflammation of the mucosa that generally spares the deeper layers of the bowel wall. Crypt abscesses, in which degenerated intestinal crypts are filled with neutrophils, also are typical of ulcerative colitis (Rubin and Farber, supra, 1994).

In comparison with Crohn's disease, which is a patchy disease with frequent sparing of the rectum, ulcerative colitis is characterized by a continuous inflammation of the colon that usually is more severe distally than proximally. The inflammation in ulcerative colitis is superficial in that it is usually limited to the mucosal layer and is characterized by an acute inflammatory infiltrate with neutrophils and crypt abscesses. In contrast, Crohn's disease affects the entire thickness of the bowel wall with granulomas often, although not always, present. Disease that terminates at the ileocecal valve, or in the colon distal to it, is indicative of ulcerative colitis, while involvement of the terminal ileum, a cobblestone-like appearance, discrete ulcers or fistulas suggest Crohn's disease. Characteristics that serve to distinguish Crohn's disease from ulcerative colitis are summarized in Table 1 (Rubin and Farber, supra, 1994).

As used herein, the term "patient with Crohn's disease" is synonymous with "patient with CD" and means a patient having a characteristic feature from at least two of the following categories: clinical, endoscopic, radiographic and histopathologic. As used herein, a characteristic clinical feature is perforating or fistulizing disease; or an obstructive symptom secondary to small bowel stenosis or stricture. As used herein, a characteristic endoscopic feature is a deep linear or serpiginous ulceration; a discrete ulcer in normal-appearing mucosa; cobblestoning; or discontinuous or asymmetric inflammation. As used herein, a characteristic radiographic feature is segmental disease (skip lesion); a small bowel or colon stricture; stenosis or fistula. As used herein, a characteristic histopathologic feature is submucosal or transmural inflammation; multiple granulomas; marked focal cryptitis or focal chronic inflammatory infiltration within and between biopsies; or a skip lesion, including histologic rectal sparing in the absence of local therapy.

TABLE 1

| Feature | Crohn's Disease | Ulcerative Colitis |
| --- | --- | --- |
| Macroscopic | | |
| Thickened bowel wall | Typical | Uncommon |
| Luminal narrowing | Typical | Uncommon |
| "Skip" lesions | Common | Absent |
| Right colon predominance | Typical | Absent |
| Fissures and fistulas | Common | Absent |
| Circumscribed ulcers | Common | Absent |
| Confluent linear ulcers | Common | Absent |
| Pseudopolyps | Absent | Common |
| Microscopic | | |
| Transmural inflammation | Typical | Uncommon |
| Submucosal fibrosis | Typical | Absent |
| Fissures | Typical | Rare |
| Granulomas | Common | Absent |
| Crypt abscesses | Uncommon | Typical |

As used herein, the term "features of ulcerative colitis" or "features of UC" means clinical features of left-sided colonic disease accompanied by a characteristic endoscopic or histopathologic feature of UC. Clinical features of left-sided colonic disease, as used herein, are rectal bleeding, urgency and tenesmus. The rectal bleeding can be accompanied by mucus discharge. An additional typical clinical feature can be treatment with topical therapy or recommended or performed total or near-total colectomy. A characteristic endoscopic feature of UC, which when present with clinical features of left-sided colonic disease indicates features of ulcerative colitis, is inflammation that is more severe distally than proximally or continuous inflammation. An additional typical endoscopic feature can be inflammation extending proximally from the rectum or shallow ulcerations or the lack of deep ulcerations. A characteristic histopathologic feature of UC, which when present with clinical features of left-sided colonic disease indicates features of ulcerative colitis, is homogeneous, continuous, predominantly superficial inflammation or a lack of "focality" within biopsy specimens. An additional typical histopathologic feature can be a crypt abscess or the lack of granulomas. Characteristic clinical, endoscopic and histopathologic features of ulcerative colitis are summarized in Table 2.

Patients with chronic inflammatory bowel disease generally are characterized as having either Crohn's disease or ulcerative colitis to describe specific patterns of disease, to predict outcomes based on expected natural histories, and to help guide medical and surgical treatment strategies. Clinical, endoscopic, and histopathologic criteria, as discussed above, have been developed to classify patients into one or the other category. However, overlap between CD and UC also has been demonstrated at a variety of levels by clinical, immunological and genetic studies, for example. Furthermore, CD and UC each can encompass a number of distinct conditions affecting the gastrointestinal tract, with different clinical subtypes being classified together as CD or UC because they present with similar symptoms. The present invention is directed to the discovery that such a clinical subtype, in particular a clinical subtype of CD with features of ulcerative colitis, can be diagnosed using perinuclear anti-neutrophil cytoplasmic antibodies (pANCA).

In one embodiment, present invention provides a method of diagnosing a clinical subtype of CD by determining whether pANCA is present in a patient with CD, by obtaining a serum sample from the patient with CD; determining whether ANCA is detectable in patient sera diluted at least about 100-fold and assaying for the presence or absence of a pANCA staining pattern, where detection of ANCA in patient sera diluted at least about 100-fold and the presence of a pANCA staining pattern indicate the presence of pANCA, provided that detection of ANCA is not by histological means.

Anti-neutrophil cytoplasmic antibodies that produce a perinuclear staining pattern are elevated in 68–80% of UC patients and less frequently in CD and other disorders of the colon. Serum titers of ANCA are elevated regardless of clinical status and, thus, do not reflect disease activity. High levels of serum ANCA also persist in patients five years post-colectomy. Although pANCA is found only very rarely in healthy adults and children, healthy relatives of UC patients have an increased frequency of pANCA, indicating that pANCA may be an immunogenetic susceptibility marker.

Serum antibodies to cytoplasmic components of a neutrophil can be detected, for example, using indirect immunofluorescence microscopy of alcohol-fixed neutrophils. ANCA activity has been divided into two broad categories: cytoplasmic neutrophil staining (cANCA) and a perinuclear to nuclear staining or cytoplasmic staining with perinuclear highlighting (pANCA). The term "anti-neutrophil cytoplasmic antibody" is synonymous with "ANCA" and encompasses both pANCA and cANCA. As used herein, the term "perinuclear anti-neutrophil cytoplasmic antibody" is synonymous with "pANCA" and refers to an antibody that reacts specifically with a neutrophil to give perinuclear to nuclear staining or cytoplasmic staining with perinuclear highlighting. The term pANCA-positive, when used in reference to a patient, means a patient having pANCA. The term "pANCA staining pattern" means a perinuclear to nuclear staining pattern or a cytoplasmic staining pattern with perinuclear highlighting that distinguishes pANCA from, for example, cANCA.

TABLE 2

| A. Clinical features of left-sided colonic disease | 1. Rectal bleeding possibly accompanied by mucus discharge |
| --- | --- |
| | 2. Urgency |
| | 3. Tenesmus |
| | 4. Treatment with topical therapy |
| | 5. Recommended or performed total or near-total colectomy |
| B. Endoscopic features of UC | 6. Inflammation that is more severe distally than proximally |
| | 7. Continuous inflammation |
| | 8. Inflammation extending proximally from the rectum |
| | 9. Shallow ulcerations or lack of deep ulcerations |
| C. Histopathologic features of UC | 10. Homogeneous, continuous, predominantly superficial inflammation |
| | 11. Lack of "focality" within biopsy specimens |
| | 12. Crypt abscesses |
| | 13. Lack of granulomas |

Previous studies have consistently shown ANCA reactivity in a small portion of patients with Crohn's disease. The reported prevalence varies from 0 to 43% with most studies reporting that between 10–30% of CD patients express ANCA (see, for example, Saxon et al., supra, 1990; Cambridge et al., Gut 33:668–674 (1992); Pool et al., Gut 3446–50 (1993); and Brokroelofs et al., Dig. Dis. Sci. 39:545–549 (1994).

The pANCA-positive subtype of Crohn's disease does not correlate with traditional CD subgroups based on, for example, location of disease (small bowel only, colon only, or small bowel and colon); extent of disease; duration of illness; disease activity; medical therapy; or surgical history (Cambridge et al., supra, 1992; Pool et al., supra, 1993; Brokroelofs et al., supra, 1994). Previous work has suggested that ANCA expression in CD patients may be related to colonic disease (Sung et al., Dig. Dis. Sci. 39:886–892 (1994); Proujansky et al., J. Pediatr. Gastroenterol. Nutr. 17:193–197 (1993); and Patel et al., Br. J. Surg. 81:724–726 (1994)). However, as disclosed herein, the majority of CD patients with colonic disease are not pANCA-positive, and the presence of colonic disease alone does not characterize the pANCA-positive subtype of CD patients (see Example IB). As disclosed herein, the presence of pANCA in CD is instead diagnostic of features of ulcerative colitis such as left-sided colonic disease in which the distal portion of the colon is more severely inflamed than the proximal portion and clinical symptoms of left-sided colonic inflammation such as rectal bleeding (see FIG. 2).

In a previous study, biopsy specimens from two Crohn's disease patients, which had a pANCA staining pattern as determined by indirect immunofluorescence, contained features of both UC and CD (Hardarson et al., Am. J. Clin. Pathol. 99:277–281 (1993)). Therefore, previous work has suggested in a very small sample that a pANCA staining pattern in a CD patient is consistent with endoscopic features of ulcerative colitis. However, the present invention is directed to determining whether pANCA is present by detection of ANCA in patient sera diluted at least 100-fold in combination with the presence of a pANCA staining pattern, provided that detection of ANCA is not by histological means. In contrast, Hardarson et al. performed immunofluorescence to assay for a pANCA staining pattern and to titer patient sera. The use of histological means, including cell staining methods such as indirect immunofluorescence, for determining whether ANCA is detectable in patient sera diluted at least about 100-fold are explicitly excluded from the present invention. In addition, the present invention is directed to the discovery that the presence of pANCA indicates a clinical subtype of CD with features of UC, where these features include clinical features as well as endoscopic or histopathologic features. Clinical features of UC had not been associated with the presence of pANCA in a patient with CD prior to the present invention.

A clinical subtype of CD with features of ulcerative colitis indicates overlap between CD and UC previously has been demonstrated. Such a clinical subtype is consistent with the relatively frequent co-occurrence of CD and UC within the same family, which indicates that these two forms of IBD, or a subtype of each disease, share a common genetic background. The familial co-occurrence of CD and UC has suggested that three genetically distinct forms of IBD exist: CD alone; UC alone and a third leading to both CD and UC (Toyoda et al., Gastroenterol. 104:741–748 (1993)).

A subtype of CD patients expressing ANCA previously has been shown to have an increased frequency of familial co-occurrence of CD and UC (Yang et al., Gastroenterol. 109:440–448 (1995)). However, in this analysis, serum ANCA was measured without determining if the ANCA was associated with a pANCA staining pattern. Furthermore, in contrast to the present invention, Yang et al., supra, 1995, demonstrated that a subgroup of ANCA-positive CD patients have family members with ulcerative colitis, but do not provide a method of diagnosing a clinical subtype where features of both UC and CD are present within the same patient.

Methods useful in determining the presence of pANCA in a patient with CD are described herein (see Example IA) and are known in the art. The presence of pANCA can be determined using a sample obtained from any biological fluid such as, for example, whole blood, plasma or other bodily fluid or tissue having pANCA, preferably serum. When multiple samples are used in an assay for determining the presence of pANCA, it is preferred that the same type of biological fluid or tissue is used for each sample. As used herein, the term "patient" means any animal capable of producing pANCA including, for example, a human, non-human primate, rabbit, rat or mouse. A sample to be assayed for the presence of pANCA can be obtained from any such patient.

A serum sample diluted at least about 100-fold is particularly useful in the methods of the invention. As disclosed herein, the presence of pANCA in a patient with CD is preferably determined by obtaining a serum sample from the patient with CD; determining whether ANCA is detectable in patient sera diluted at least about 100-fold and assaying for the presence or absence of a pANCA staining pattern, where detection of ANCA in patient sera diluted at least about 100-fold and the presence of a pANCA staining pattern indicate the presence of pANCA, provided that the detection of ANCA is not by histological means. Numerous studies have used indirect immunofluorescence alone to detect the presence of serum ANCA, thereby determining whether pANCA is present simply on the basis of a pANCA staining pattern. Furthermore, where a quantitative assay has been relied upon in addition to a pANCA staining pattern, detection of ANCA has been determined using a relatively high concentration of patient sera, such as a 20-fold or 40-fold dilution of sera, for example. In contrast, the present invention is directed to the novel discovery that the presence of pANCA, as determined rigorously by both detection of ANCA in patient sera diluted at least about 100-fold and the presence of a pANCA staining pattern, is diagnostic of a clinical subtype of CD with features of ulcerative colitis, provided that detection of ANCA in patient sera is not by histological means.

As used herein, the term "histological means," when used in reference to detection of ANCA or detection of a first complex of antigen and ANCA, refers to a technique for studying the structure of a cell or tissue using staining and microscopy. Histological means, which encompass techniques such as immunocytochemistry and indirect immunofluorescence, can distinguish CANCA and pANCA staining patterns and, thus, are useful in assaying for the presence or absence of a pANCA staining pattern, for example. However, histological means, which typically are subjective, are not useful for rigorously determining whether ANCA is detectable in patient sera diluted at least about 100-fold. The use of histology, as defined herein, for determining whether ANCA is detectable in patient sera diluted at least about 100-fold are explicitly excluded from the present invention. Similarly, the present invention explicitly excludes the use of histological means to detect the presence or absence of a first complex of antigen and ANCA.

It is recognized that determining whether ANCA is detectable in patient sera diluted at least about 100-fold can be performed prior to, following or concurrent with assaying for the presence or absence of a pANCA staining pattern. Thus, for example, an immunofluorescence assay for the presence of a pANCA staining pattern followed by an enzyme-linked immunosorbent assay for determining whether ANCA is detectable in patient sera diluted at least about 100-fold is encompassed within the methods of the invention.

Methods of determining whether ANCA is detectable in patient sera diluted at least about 100-fold are well known in the art (Harlow and Lane, *Antibodies: A Laboratory Manual* New York: Cold Spring Harbor Laboratory (1988), which is incorporated herein by reference). For example, ANCE can be detected in patient sera using a detectable reagent such as a secondary antibody labeled with a detectable enzymatic, radioisotopic, fluorescent or chemiluminescent market. Particularly useful methods include a quantitative assay such as an immunoassay, in which an antibody selective for ANCA is used to detect ANCA in patient sera. A radioimmunoassay (RIA) or enzyme-linked immunosorbent assay (ELISA), for example, is encompassed within the invention. As discussed above, the present invention explicitly excludes the use of histological means such as immunocytochemistry or immunofluorescence for determining whether ANCA is present in patient sera diluted at least about 100-fold.

An enzyme-linked immunosorbent assay (ELISA) can be useful in determining whether ANCA is present in patient sera diluted at least about 100-fold. For example, a fixed neutrophil ELISA for detection of ANCA in patient sera diluted 100-fold is described in Example IA. An enzyme that is linked to a secondary antibody selective for ANCA can be, for example, horseradish peroxidase (HRP), alkaline phosphatase (AP), β-galactosidase or urease. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm, or a urease detection system can be used with a substrate such as urea-bromocresol purple (Sigma Immunochemicals, St. Louis, Mo.). A secondary antibody linked to an enzyme is a detectable reagent useful in an ELISA and can be obtained from a number of commercial sources. For example, goat F(ab')2 anti-human IgG-alkaline phosphatase can be purchased from Jackson Immuno-Research (West Grove, Pa.).

A radioimmunoassay also can be useful in determining whether ANCA is present in patient sera diluted at least about 100-fold. A radioimmunoassay using, for example, an iodine-125 labeled secondary antibody (Harlow and Lane, supra, 1988) is encompassed within the invention.

A secondary antibody labeled with a chemiluminescent marker also can be useful for determining whether pANCA is present. Such a chemiluminescent secondary antibody is convenient for sensitive, non-radioactive detection of pANCA and can be obtained commercially from various sources such as Amersham Lifesciences, Inc. (Arlington Heights, Ill.).

In addition, a detectable reagent labeled with a fluorochrome can be useful in determining whether ANCA is present in patient sera diluted at least about 100-fold. Appropriate fluorochromes include, for example, DAPI, fluorescein, Hoechst 33258, R-phycocyanin, B-phycoerythrin, R-phycoerythrin, rhodamine, Texas red or lissamine. A particularly useful fluorochrome is fluorescein or rhodamine. A secondary antibody linked to a fluorochrome is a particularly useful detectable reagent and can be obtained commercially. For example, goat F(ab')2 anti-human IgG-FITC is available from Tago Immunologicals (Burlingame, Calif.).

A signal from the detectable reagent can be analyzed, for example, using a spectrophotometer to detect color from a chromogenic substrate; a radiation counter to detect radiation, such as a gamma counter for detection of iodine-125; or a fluorometer to detect fluorescence in the presence of light of a certain wavelength. For detection of enzyme-linked reagents, a quantitative analysis of the amount of ANCA can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

Immunoassays using a secondary antibody that binds ANCA selectively are particularly useful for determining whether ANCA is detectable in patient sera diluted at least about 100-fold. For example, an anti-Ig antibody such as anti-IgG is selective for ANCA and useful in the methods of the invention when labeled with a detectable marker such as an enzyme, fluorochrome or radioactive isotope. A useful secondary antibody is selective for the species of the ANCA to be detected. For example, if human serum is the sample to be assayed, mouse anti-human IgG can be a useful detectable reagent. In addition, a second selective binding reagent can be useful in detecting ANCA. For example, a goat anti-mouse antibody, which is selective for the class determining portion of the mouse anti-human IgG antibody, can be used in combination with mouse anti-human IgG to detect ANCA in human sera.

A secondary antibody useful in an immunoassay of the invention can be obtained commercially or by techniques well known in the art. Such an antibody can be a polyclonal or, preferably, monoclonal antibody that binds ANCA selectively. For example, IgG reactive polyclonal antibodies can be prepared using IgG or Fc fragments of IgG as an immunogen to stimulate the production of antibodies in the antisera of an animal such as a rabbit, goat, sheep or rodent, for example (Harlow and Lane, supra, 1988).

A monoclonal antibody useful in the practice of the invention can be obtained from a number of commercially available sources. In addition, an immunogen useful to generate a monoclonal antibody that binds ANCA selectively can be, for example, human IgG or a Fc fragment of human IgG, ANCA or a Fab fragment of ANCA. A hybridoma that produces a monoclonal selective for ANCA can be identified by screening hybridoma supernatants for the presence of antibodies that bind ANCA specifically (Harlow, supra, 1988). For example, such a screening method can be a radioimmunoassay or enzyme-linked immunosorbent assay using neutrophil and pANCA-positive sera, for example.

Methods of assaying for the presence or absence of a pANCA staining pattern also are well known in the art. Methods of cell staining using, for example, neutrophil, are useful for determining the subcellular localization of ANCA reactivity, thereby differentiating pANCA from cANCA. Immunocytochemistry or immunofluorescence are particularly useful for assaying for the presence of a pANCA staining pattern (Harlow and Lane, supra, 1988). An enzyme-labeled or fluorochrome labeled secondary antibody that binds ANCA selectively, such as described above, can be useful in such methods. For example, indirect immunofluorescence readily can be performed by incubating methanol-fixed neutrophil with a 1:20 dilution of human sera and detecting the complex formed with fluorescein-labeled F(ab')2 γ chain secondary antibody. The presence or absence of the pANCA staining pattern in the stained cells is visualized using fluorescence microscopy as described in Saxon et al., supra, 1990, or in Example IA.

In one embodiment, the invention provides a method of diagnosing a clinical subtype of CD by determining whether pANCA is present in a patient with CD by obtaining a serum sample from the patient with CD; contacting the serum sample diluted at least about 100-fold with antigen specific for ANCA under conditions suitable to form a first complex of antigen and ANCA; detecting the presence or absence of the first complex; contacting an appropriate dilution of the serum sample with antigen specific for ANCA under conditions suitable to form a second complex of neutrophil and ANCA; and assaying for the presence or absence of a pANCA staining pattern by detecting the presence or absence of the second complex, where the presence of the first complex and the presence of a pANCA staining pattern indicate the presence of pANCA, provided that detection of the first complex is not by histological means.

As used herein, the term "antigen specific for ANCA" is an antigen or mixture of antigens that is bound specifically by anti-neutrophil cytoplasmic antibody. For example, neutrophil is a particularly useful antigen specific for ANCA that can be obtained from a variety of sources, such as from blood derived from a human, non-human primate, rabbit, rat or mouse. Methods for preparing neutrophil are well known in the art; for example, human neutrophil can be prepared from human peripheral blood using sedimentation in 1% dextran as described in Saxon et al., supra, 1990. Preferably, neutrophil employed in the assay will have specific reactivity with the species from which the serum sample is obtained. For example, in an assay for ANCA or pANCA from a human patient, a human neutrophil is preferably employed. In addition, an antigen purified from neutrophil, which is bound specifically by ANCA, also can be an antigen specific for ANCA useful in the present invention.

The invention further provides a method of diagnosing a clinical subtype of CD by detecting an $Arg^{241}$ allele at an ICAM-1 locus in a patient with CD, where the $Arg^{241}$ allele indicates a clinical subtype of CD with features of ulcerative colitis. According to the methods of the invention, an $Arg^{241}$ allele can be detected by obtaining material from the patient with CD; preparing a nucleic acid comprising nucleotide 721 of SEQ ID NO: 1 from the material; contacting the nucleic acid with an $Arg^{241}$ allele-specific oligonucleotide probe under conditions suitable for formation of a specific hybrid between the nucleic acid and the $Arg^{241}$ allele-specific oligonucleotide probe; and assaying for the presence of the specific hybrid, where the presence of the specific hybrid indicates the $Arg^{241}$ allele.

In addition, the invention provides a method of diagnosing a pANCA-positive subtype of CD by detecting an $Arg^{241}$ allele at an ICAM-1 locus in a patient with CD, where the $Arg^{241}$ allele indicates the pANCA-positive subtype of CD. A pANCA-positive subtype of CD can be diagnosed according to the methods of the invention by obtaining material from a patient with CD; preparing a nucleic acid comprising nucleotide 721 of SEQ ID NO: 1 from the material; contacting the nucleic acid with an $Arg^{241}$ allele-specific oligonucleotide probe under conditions suitable for formation of a specific hybrid between the nucleic acid and the $Arg^{241}$ allele-specific oligonucleotide probe; and assaying for the presence of the specific hybrid, where the presence of the specific hybrid indicates the $Arg^{241}$ allele.

Inflammatory bowel disease is characterized by a failure to down-regulate the usual self-limited gut inflammatory response, suggesting that one or more of the predisposing genes could be those that determine the level of the immune response along the inflammatory pathway. Evidence for a genetic component to Crohn's disease includes consistent ethnic differences in disease frequency that cross different geographic areas; the familial occurrence of IBD; the existence of genetic syndromes that feature inflammatory bowel disease; and associations between IBD and genetic markers.

Host genetic factors involved in inflammatory bowel disease can be molecules involved in immune recognition and specificity, such as HLA or T-cell receptor alleles or immunoglobulin allotypes, termed immunospecific genes. Host genetic factors important in IBD also include inflammatory cell adhesion molecules, which are essential for interaction of circulating leukocytes with the endothelium during immune and inflammatory reactions and for B and T-cell activation.

Intracellular adhesion molecule-1 (ICAM-1), is a member of the immunoglobulin gene superfamily that plays an important role in inflammation. In vitro studies have shown that ICAM-1 is involved in transendothelial migration of neutrophils, mixed lymphocyte response, and T-cell activation. (Harlan et al., *Adhesion, Its Role in Inflammatory Disease*, New York: Freeman (1992); Springer et al., *Leukocyte Adhesion Molecules Structure. Function. and Regulation*, New York: Springer Verlag (1988); Damie et al., *J. Immunol.* 148:655–671 (1992)). In vivo studies have shown that an anti-ICAM-1 monoclonal antibody can inhibit migration of neutrophils in response to inflammation of the lung, peritoneum or myocardium (Barton et al., *J. Immunol.*

143:1278–1282 (1989); Harlan et al., supra (1992)). In particular, increased expression of ICAM-1 in colon has been observed in UC and CD (Malizia et al., *Gastroenterol.* 100:150–159 (1991)). Mice rendered deficient in ICAM-1 by gene targeting also have abnormal inflammatory responses, including impaired neutrophil emigration (Sligh et al., *Proc. Natl. Acad. Sci USA* 90:8529–8533 (1993)). Thus, induction of ICAM-1 on mononuclear phagocytes can be important in maintenance of chronic inflammation by facilitating, for example, neutrophil emigration from the vasculature or by acting as a co-stimulatory molecule in the immune response.

ICAM-1 has five immunoglobulin-like domains; domains one and three are functionally important in that they bind leukocyte integrin. A single base change, corresponding to an amino acid polymorphism, is located at codon 241 in exon 4 (immunoglobulin-like domain three). $Arg^{241}$ (AGG) or $Gly^{241}$ (GGG) can be present at this position (see, for example, Vora et al., *Genomics* 21:473–477 (1994), which is incorporated herein by reference). The present invention is directed to the discovery that the frequency of the $Arg^{241}$ ICAM-1 allele is significantly higher in the pANCA-positive subtype of CD than in cANCA-positive or ANCA-negative subtypes. Thus, the invention provides a method of diagnosing a pANCA-positive subtype of CD by detecting an $Arg^{241}$ allele at an ICAM-1 locus in a patient with CD, where the $Arg^{241}$ allele indicates the pANCA-positive subtype of CD.

As disclosed herein, Crohn's disease patients can be subtyped according to the presence of pANCA, where the presence of pANCA is defined by detection of ANCA in patient sera diluted at least about 100-fold and the presence of a pANCA staining, provided that detection of pANCA is not by histological means. As described in Example II, stratification of CD patients according to pANCA status reveals a significant association of the $Arg^{241}$ allele with the pANCA-positive subtype of CD. The results summarized in Table 6 indicate that 50% of pANCA-positive CD have the ICAM-1 $Arg^{241}$ allele as compared to only about 15% of pANCA-negative CD patients. The presence of pANCA, as discussed above, can be used to diagnose a clinical subtype of CD with features of ulcerative colitis. Thus, the association of the ICAM-1 $Arg^{241}$ allele with pANCA-positive CD also provides the basis for a method of diagnosing a clinical subtype of CD with features of ulcerative colitis by detecting an $Arg^{241}$ at an ICAM-1 locus.

As used herein, the term "material" means any biological matter from which a nucleic acid can be prepared. For example, the term material encompasses whole blood, plasma or other bodily fluid or tissue that contains nucleic acid. A preferred material is patient sera, which can be obtained readily by non-invasive means and used to prepare a nucleic acid for the diagnosis of Crohn's disease according to the methods of the invention.

As used herein, the term "nucleic acid" means a polynucleotide such as deoxyribonucleic acid (DNA) or ribonucleic acid (RNA). A nucleic acid can be either single-stranded or double-stranded. To practice the methods of the invention, a particularly useful nucleic acid is genomic DNA, complementary DNA or messenger RNA. The term nucleic acid molecule, as used herein, encompasses a nucleic acid or oligonucleotide.

As used herein, the term "locus" means a physical location, place or position occupied by a particular gene on a chromosome. As used herein, the term "ICAM-1 locus" means any nucleic acid or chromosomal segment that encodes ICAM-1 or that influences expression of any ICAM-1 gene.

As used herein, the term "allele" means an alternative gene sequence that occupies the same chromosomal locus, with an alternative gene sequence including any modification or variation of a gene.

An allele at a polymorphic locus, such as the $Arg^{241}$ allele, can be detected by a variety of methods including assays using the polymerase chain reaction (PCR). Allele-specific oligonucleotide hybridization (see Mullis et al. (ed.), *The Polymerase Chain Reaction* Boston: Birkhäuser (1994), which is incorporated herein by reference), denaturing gradient gel electrophoresis (see, for example, Innis et al., *PCR Protocols: A Guide to Methods and Application*, San Diego: Academic Press, Inc. (1990)) and restriction fragment length polyphormism based methods (Sambrook et al., supra, 1989), for example, are well known in the art and encompassed within the invention.

As used herein, the term "$Arg^{241}$ allele-specific oligonucleotide probe" means a nucleic acid molecule that will form a specific hybrid, under appropriate conditions, with a nucleic acid including nucleotide 721 of SEQ ID NO: 1, such that one allele is distinguished from another allele. Thus, for example, an $Arg^{241}$ allele-specific oligonucleotide probe will form a hybrid with a nucleic acid including an adenine at nucleotide 721 of SEQ ID NO: 1, but will not form a hybrid with a nucleic acid including a guanine at nucleotide 721 of the sequence shown in FIGS. 4A–4D (SEQ ID NO: 1). Appropriate conditions for formation of a specific hybrid such that, for example, a single nucleotide mis-match between a nucleic acid and an allele-specific oligoprobe will preclude formation of a hybrid are well known in the art (Sambrook et al., supra, 1989) and are described in Example II.

An $Arg^{241}$ allele-specific oligonucleotide probe preferably is a nucleic acid having from about seven to about thirty-five nucleotides. More preferably, an $Arg^{241}$ allele-specific olignucleotide probe has from about twelve to about thirty-five nucleotides and most preferably has from about seventeen to about twenty-five nucleotides. An $Arg^{241}$ allele-specific oligonucleotide probe can be a nucleic acid comprising, for example, CTGCACG (SEQ ID NO: 2); TGCACGG (SEQ ID NO: 3); GCACGGG (SEQ ID NO: 4); CACGGGC (SEQ ID NO: 5); ACGGGCT (SEQ ID NO: 6); CGGGCTG (SEQ ID NO: 7); and GGGCTGT (SEQ ID NO: 8), or a complementary sequence thereto. A particularly useful $Arg^{241}$ allele-specific oligonucleotide probe is 5' TCCCTGGACAGGCTGTTCC3' (SEQ ID NO: 9).

As used herein, the term "under conditions suitable for formation of a specific hybrid" means any set of parameters, physical conditions (such as temperature) or chemical conditions (such as pH, salt concentration) such that an oligonucleotide probe will form a hydrogen bonded, sequence-specific association with the nucleic acid target sequence to which the oligonucleotide probe is complementary. Defining such parameters and conditions is routine to one skilled in the art, and for example is described in Sambrook et al., supra, 1989, and Mullis et al., supra, 1994, both of which have been incorporated herein by reference.

The following examples are intended to illustrate but not limit the present invention.

EXAMPLE I

Comparison of the clinical feature of pANCA-positive and pANCA-negative CD patients This example demonstrates that the pANCA status of Crohn's disease patients correlates with a clinical subtype of Crohn's disease having features of ulcerative colitis.

A. Determination of patient ANCA status by ELISA and indirect immunofluorescence assay Presence of ANCA was determined by fixed neutrophil ELISA A fixed neutrophil enzyme-linked immunosorbent assay was used to detect ANCA as described in Saxon et al., supra, 1990, which is incorporated herein by reference, and all samples were analyzed in a blinded fashion. Microliter plates were coated with $2.5 \times 10^5$ neutrophils per well and treated with 100% methanol to fix the cells. Cells were incubated with 0.25% bovine serum albumin (BSA) in phosphate-buffered saline to block nonspecific antibody binding. Next, control and coded sera were added at a 1:100 dilution to the bovine serum/phosphate-buffered saline blocking buffer. Alkaline phosphatase conjugated goat $F(ab')_2$ anti-human immunoglobulin G ($\gamma$-chain specific) antibody (Jackson Immunoresearch Labs, Inc., West Grove, Pa.) was added at a 1:1000 dilution to label neutrophil bound antibody. A p-nitrophenol phosphate substrate solution was added and color development was allowed to proceed until absorbance at 405 nm in the positive control wells was 0.8–1.0 optical density units greater than the absorbance in blank wells. The results were expressed as percent of standard binding with pANCA-positive defined as greater than two standard deviations (SD) above mean of control. Titers were also determined.

Indirect immunofluorescence assay for determination of ANCA staining pattern

Indirect immunofluorescent staining was performed on samples that were ANCA-positive by ELISA to determine whether the predominant staining pattern was perinuclear (pANCA) or cytoplasmic (cANCA). Glass slides containing approximately 100,000 neutrophils per slide were prepared by cytocentrifugation (Shandon Cytospin, Cheshire, England) and they were fixed in 100% methanol, air-dried, and stored at $-20°$ C. The fixed neutrophils were incubated with human sera were diluted (1:20), and the reaction was visualized with fluorescein-labeled $F(ab')_2$ $\gamma$ chain-specific antibody as described in Saxon et al., supra, 1990. The slides were examined using an epifluorescence-equipped Olympus BH-2 microscope (Olympus, Lake Success, N.Y.).

Characteristics of Anti-Neutrophil Cytoplasmic Antibodies from CD patients

Serum ANCA was detected in 38/69 (55%) of the CD study population. ANCA-positive CD patients demonstrated a slight predominance of cytoplasmic staining (53%) as compared to periplasmic staining (47%), although this did not reach statistical significance ($p_c=0.75$). The mean ELISA binding level of the pANCA-positive CD serum samples (41±6) was higher than those that were cANCA-positive (16±1; p<0.000001) or ANCA-negative (6±1; p<0.000001) (see FIG. 1). Provided at the right of FIG. 1 for comparison are mean binding levels of historical ANCA-positive controls as described by Duerr et al., *Gastroenterol.* 100:1590–1596 (1991), which is incorporated herein by reference. The pANCA-positive and cANCA-positive subgroups are denoted "p" and "c," Comparison of the mean ELISA binding levels of the pANCA-positive, cANCA-positive, and ANCA-negative CD subgroups to historical means for ANCA+ UC patients from data by Duerr et al., supra, 1991 (pANCA-positive UC:65±6; cANCA+ UC:36±2), indicated that ANCA is present at lower levels in ANCA+ CD patients than ANCA+ UC patients. The mean titer of the pANCA-positive CD subgroup (512±87) was higher than that of the cANCA+ subgroup (227±25) (p=0.0024).

Statistical analysis

Statistical analysis was performed using Student's t tests for comparisons of quantitative variables between two groups. Yate's continuity corrected $\chi^2$ tests, denoted by $p_c$, were used for comparisons of qualitative variables between two or more groups. When the expected number of a cell is less than 5, Fisher's exact tests were also calculated for comparisons between two proportions and corresponding p-values were denoted by $p_{Fisher's\ exact}$. Log transformations were performed for ANCA titers to obtain a normal distribution for hypothesis testing.

B. Clinical symptoms of pANCA-positive and pANCA-negative CD patients

Clinical assessment and characterization of Crohn's disease patients

Clinical information for 69 CD patients was collected by chart review and patient interview by clinical investigators who were blind to individual patient ANCA status. Epidemiological data included: age, age at onset of IBD symptoms, disease duration, gender, ethnicity, and family history of IBD. For each patient, all areas of endoscopically, surgically, histopathologically, or radiographically documented inflammation, stricturing, fistulization, or perforation were recorded. For purpose of analysis, anatomic location of disease was further grouped into categories of "small bowel disease only," "ileocolonic disease," and "colonic involvement only." Signs and symptoms associated with active Crohn's disease were noted, including: obstructive symptoms, diarrhea, bleeding and mucus discharge, urgency, tenesmus, perianal abscess or fistula, anal fissures or strictures, as well as extraintestinal manifestations of IBD. Pharmacological interventions were grouped to reflect the use of sulfasalazine or oral 5-ASA products; immunomodulatory agents such as 6-mercaptopurine/azathioprine, methotrexate, cyclosporin or anti-TNF antibody therapy; IBD-directed antibiotic therapy; or topical therapy for distal colonic disease such as enemas, foams or suppositories. Steroid use was noted and further quantified into estimated total years of systemic corticosteroid exposure, termed "steroid years." The number, type, and reason for all IBD-related surgeries also was recorded.

CD patients were examined for "features of ulcerative colitis." Features of ulcerative colitis were defined as clinical features of left-sided colonic disease, including a combination of the typical left-sided features outlined in Table 2, section A, which are further corroborated by the endoscopic or histopathologic features listed in Table 2, sections B and C. Patients exhibiting these features characteristic of left-sided or distal UC, have features of UC.

Pathology reports were obtained in 93% of the total study population (100%, 85% and 94% of pANCA-positive, cANCA-positive, and ANCA-negative CD subgroups, respectively). Actual biopsies or surgical specimens were available for review by one of two pathologists with IBD expertise in 42% of the overall CD population (61%, 30%, and 35% of pANCA-positive, cANCA-negative, and ANCA-negative CD subgroups, respectively). Special attention was paid to the character of inflammatory process (homogeneous/continuous versus focal inflammation within and between biopsy specimens), the depth of inflammation (superficial versus extension into submucosa or transmural inflammatory process), and the presence or absence of granulomas and crypt abscesses.

Distribution of clinical and epidemiological characteristics of Crohn's disease stratified according to ANCA status A comparison of the clinical and epidemiological characteristics of the pANCA-positive CD, cANCA-positive CD, and ANCA-negative CD subgroups is depicted in Table 3. No significant relationship was detected between the presence of pANCA or cANCA and age, age of onset, disease duration, gender, or family history of IBD ($p_c>0.05$). More patients were of Jewish descent in the cANCA-positive subgroup than in the ANCA-negative group ($p_c=0.025$). There was no significant difference in frequency of perforating or fistulizing disease in the pANCA-positive subgroup ($p_c>0.10$). There was no significant difference in disease severity between the subgroups, as reflected by numbers of surgeries or years of exposure to systemic steroid therapy ($p_c>0.05$). The majority of CD patients in all three groups required immunomodulation.

Figure 2:
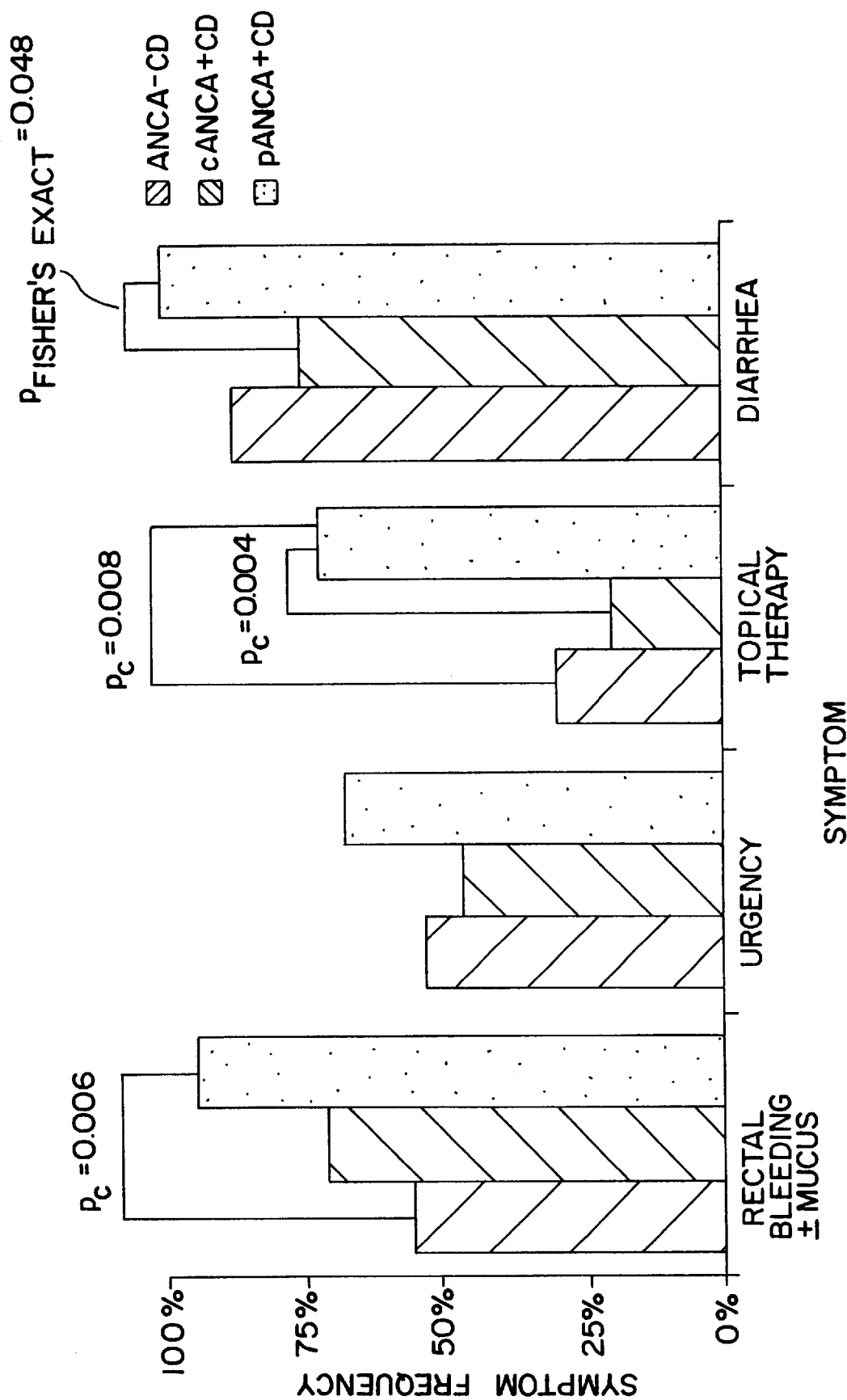
FIG. 2 shows the clinical symptoms of a Crohn's disease study population of 69 patients. The differences between groups without p-values are not statistically significant.

Frequency of clinical symptoms of left-sided colonic inflammation in pANCA-positive Crohn's disease patients Crohn's disease patients who were pANCA-positive more often exhibited rectal bleeding and mucus discharge, than did the ANCA-negative CD subgroup ($p_c=0.006$) or the cANCA-positive CD subgroup ($p_{Fisher's\ exact}=0.09$) as shown in FIG. 2. A trend towards increased urgency was also evident in the pANCA-positive subgroup. The higher prevalence of left-sided symptoms in the pANCA-positive subgroup as compared with the ANCA-negative and cANCA-positive subgroups was reflected in the higher percent of pANCA-positive patients having been treated with topical agents ($p_c=0.008$ and $p_c=0.004$, respectively). A greater number of pANCA-positive CD patients experienced diarrhea than those in the cANCA-positive CD ($p_{Fisher's\ exact}=0.048$) and the ANCA-negative CD ($p_c>0.112$) subgroups. Thus, symptoms of left-sided colonic inflammation such as rectal bleeding and mucous discharge, urgency, and treatment with local topical 5-ASA or steroid therapies were more often present in pANCA-positive CD patients. Characteristic features of Crohn's disease exhibited by the pANCA+ CD patients are highlighted in Table 4.

pANCA-positive Crohn's disease patients do not have isolated small bowel inflammation The anatomic location of documented Crohn's disease involvement for the pANCA-positive, cANCA-positive, and ANCA-negative CD subgroups was

TABLE 4

| Patient | Confirmed Small Bowel Disease* | Perianal Fistula Abscess | Other Fistula/Abscesses | Anal Disease | Endoscopic & Histopatholgic | Submucosal or Transmural Inflammation | Granulomas | Other |
|---|---|---|---|---|---|---|---|---|
| 1 | String sign in distal TI | | | Indurated, Inflamed | Cobblestoning; Endoscopic skip lesions | | | oral AU's |
| 2 | Cobblestoning of distal TI; Anastomotic stenosis | F | TI perforation; 10 yrs later-Anastomotic A | | Anastomotic ulcerations & S; Asymmetric inflammation; Deep fissures; Linear ulcers | Y | Y | s |
| 3 | | | | | | | Y | |
| 4 | | Multiple F's & A's | Recto-vaginal | Induration; S; Fissure; Tags | Linear/serpiginous ulcerations; Tight S in sigmoid | | Y | |
| 5 | | | | | Endoscopic & histologic skip lesions | Y | | |
| 6 | | | | | Endoscopic skip lesions | Y | Y | |
| 7 | Multiple high-grade ileal S's following two resections for SBO | | | | Endoscopic skip lesions | | | |
| 8 | | | | | Deep, discrete ulcers within normal mucosa; Discontinuous, asymmetric inflammation | Y | | |
| 9 | | F | | Fissure | Histologic skip regions; Cobblestoning; Deep & linear ulcers; Asymmetric inflammation | Y | Y | |
| 10 | | | | | Histologic skip lesions | Y | Y | |
| 11 | | | | | Endoscopic & histologic skip lesions | Y | Y | |
| 12 | Ulcerations in TI; Recurrent anastomotic ulceration | Multiple F's | Enterocutaneous A/F | Tags | Discontinuous, asymmetric inflammation; Cobblestoning | Y | Y | oral AU's |
| 13 | | F | Peripouch F/A | Anal ulcers; Fissure | Recurrence in pouch; Cobblestoning; Stricture at pouch-anal anastomosis | | | |
| 14 | | | | | Deep, discrete ulcers within normal mucosa; Discontinuous, asymmetric inflammation | | | |
| 15 | Inflamed, stenotic TI | | "Microperforation" | | Undermining, serpiginous ulcers; Discontinuous, asymmetric inflammation; Cobblestoning | Y | | oral AU's |
| 16 | TI ulcerations, nodularity and stenosis; Jejunal filing defects | | | | | | | oral AU's |
| 17 | Linear ulcerations and stenosis in distal ileum | | | | | | | |
| 18 | TI ulceration & S | | | | Discrete ulcers within normal mucosa; Endoscopic skip lesions; Deep linear ulcerations Discrete ulcers within normal mucosa; Histologic skip lesions; Deep linear ulcerations | | | oral AU's |
| | 8/18 (44%) | 5/18 (26%) | 5/18 (28%) | 4/18 (22%) | 16/18 (89%) | 10/18 (56%) | 9/18 (50%) | 5/18 (28%) |

TI = Terminal Ileum; S = stricture; SB = Small bowel; SBO = Small bowel obstruction; F = Fistual; A = Abscess; AU = Aphthous ulcers
*Small bowel disease confirmed by radiographic, endoscopic, and/or surgical evaluations categorized into "small bowel disease only", "ileocolonic disease", and "colonic involvement only." Ileocolonic involvement was observed in fifty percent of pANCA-positive CD patients, and the disease was limited to the colon in the other fifty percent. No patient in the pANCA-positive CD subgroup had disease limited to the small bowel. Similarly, small bowel obstructive symptoms were exhibited less frequently in the pANCA-positive subgroup than in the other subgroups, although this difference did not reach statistical significance.

Figure 3:
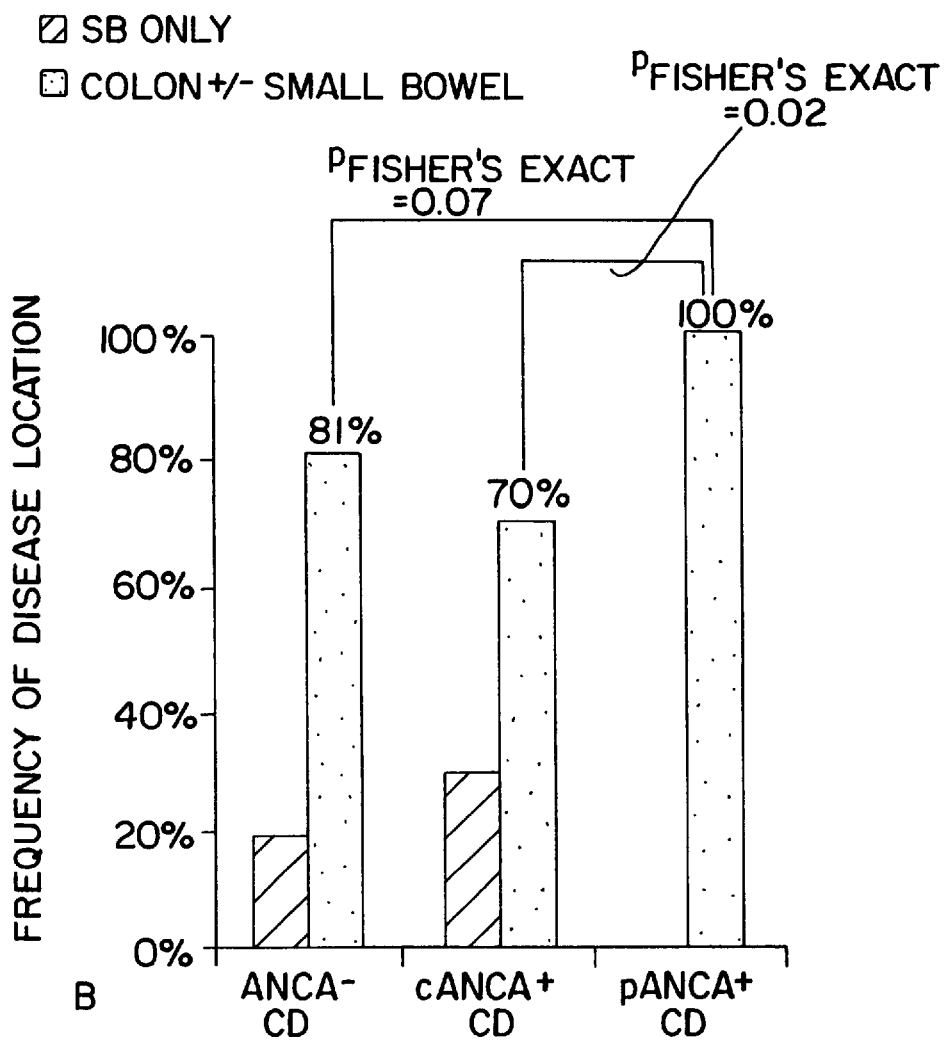
FIG. 3 shows the anatomic distribution of disease by ANCA-negative, cANCA-positive and pANCA-positive CD subgroups. Colonic involvement, with or without small bowel disease, was present in the majority of CD patients within each subgroup.

Expression of serum pANCA is not related solely to the presence of colonic disease Colonic inflammation such as ileocolonic disease or colonic involvement only was present in 83% of the CD study population as shown in FIG. 3. The majority of patients in each subgroup had colonic involvement: 100% of the pANCA-positive CD subgroup, 70% of the cANCA-positive CD subgroup, and 81% in the ANCA-negative CD subgroup). There was no statistically significant difference between the proportion of pANCA-positive and ANCA-negative patients with colonic disease ($p_{Fisher's\ exact}$=0.07). Of all CD patients with colonic involvement, 32% were pANCA-positive, while the majority of CD patients with colitis (68%) did not express serum pANCA. Thus, the expression of serum pANCA, is not related solely to the presence of colonic disease.

Left-sided colitis is present in all pANCA-positive Crohn's disease patients

Endoscopic or histopathologic inflammation of the rectum or sigmoid colon was present in every pANCA-positive CD patient. The frequency of endoscopically or histopathologically documented left-sided colitis was significantly different when compared to either the ANCA-negative ($p_c$=0.002) or cANCA+ ($p_{Fisher's\ exact}$=0.001) subgroup. There was no difference between the latter two subgroups ($p_c$=1).

pANCA-positive CD patients have features of ulcerative colitis

The absence of Crohn's involvement limited to the small bowel and the clinical expression of symptoms of left-sided colonic inflammation, along with documented left-sided colitis are all features consistent with ulcerative colitis. In addition to their other features of CD, a subset of the CD study population was noted to have features of ulcerative colitis. For these patients with Crohn's disease to be considered to have features of ulcerative colitis, they needed to, at minimum, have rectal bleeding, urgency and tenesmus, which are clinical features of left-sided colonic disease, in combination with a characteristic endoscopic feature (inflammation that is more severe distally than proximally or continuous inflammation or a characteristic histopathologic feature (homogeneous, continuous, predominately superficial inflammation or lack of "focality" within biopsy specimens). Forty-six percent of all CD patients exhibiting features of ulcerative colitis expressed serum pANCA. In contrast, none of the 30 CD patients lacking these features were pANCA-positive. This difference was highly significant. One hundred percent of pANCA-positive CD patients exhibited features of ulcerative colitis. The number of patients having features of ulcerative colitis was 18/18 (100%) in the pANCA-positive CD subgroup; 9/20 (45%) in the cANCA-positive CD subgroup and 12/31 (39%) of patients in the ANCA-negative CD subgroup (see Table 5). Thus, the percent of pANCA-positive CD patients with features of ulcerative colitis was significantly higher than the percent of patients meeting the criteria in either the cANCA-positive or ANCA-negative subgroups.

TABLE 5

| Subtype of CD | ANCA-negative CD | cANCA-positive CD | pANCA-positive CD |
|---|---|---|---|
| Frequency of features of UC | 39% | 45% | 100% |

EXAMPLE II

Frequency of the $Arg^{241}$ allele of ICAM-1 in subtypes of with Crohn's disease stratified according to ANCA status This example demonstrates that the pANCA status of Crohn's disease patients correlates with the presence of the $Arg^{241}$ allele of Intracellular adhesion molecule-1 (ICAM-1).

A. The ICAM-1 $Arg^{241}$ allele is associated with the pANCA-positive subtype of CD Crohn's disease patients were subgrouped according to ANCA status and evaluated for the presence of the ICAM-1 $Arg^{241}$ allele. pANCA-positive patient status was determined as described in Example IA with both a fixed neutrophil ELISA using a 100-fold dilution of patient sera and immunofluorescence to determine the perinuclear or cytoplasmic staining pattern. CD patients that were determined to be pANCA-positive (n=14) had a significantly increased frequency of the $Arg^{241}$ allele (50%) as compared with pANCA-negative CD patients (15.7%; n=108) (p=0.002). The frequency of the $Arg^{241}$ allele in the cANCA-positive CD patient subgroup (15.4%; n=13) was similar to that of the ANCA-negative CD patient subgroup (15.8%; n=95) (p=0.97). The cANCA-positive and ANCA-negative CD subgroups had an $Arg^{241}$ allele frequency which was comparable to that of normal controls (13.9%; n=72) or ANCA-positive UC patients (cANCA-positive: 8.3%; n=12 and pANCA-positive: 11.1%; n=72). These results are summarized in Table 6.

TABLE 6

| Subtype | Number of Patients | Frequency of $Arg^{241}$ Allele |
|---|---|---|
| pANCA-positive CD | 14 | 50% |
| pANCA-negative CD | 108 | 15.7% |
| cANCA-positive CD | 13 | 15.4% |
| ANCA-negative CD | 95 | 15.8% |
| ANCA-positive UC | 84 | 19.4% |
| Control | 72 | 13.9% |

B. Detection of the $Arg^{241}$ allele

Amplification of genomic nucleic acid including the ICAM-1 $Arg^{241}$ allele.

The ICAM-1 $Arg^{241}$ allele was detected by a polymerase chain reaction (PCR) allele-specific oligonucleotide technique as described in Vora et al., *Genomics* 21:473–477 (1994), which is incorporated herein by reference. A pair of primers, 5'GATTGAAGAAGCCAGCAG3' (SEQ ID NO: 10) and 5'GTCGTTGCCATAGGTGAC3' (SEQ ID NO: 11), which flank codon 241, were used to amplify patient DNA as follows:

Genomic DNA was amplified using 20 μl PCR reactions under the following conditions: 10 mM Tris-HCl at pH 8.3, 50 mM KCl, 1.5 mM $MgCl_2$, 200 μM each dNTP, 10 μM each primer, 50 ng of genomic DNA, and 0.5 units of AmpliTaq polymerase (Perkin-Elmer Cetus, Norwalk, Conn.). The DNA was amplified for 40 cycles: 94° C. for 30 seconds 55° C. for 30 seconds, and 72° C. for 45 seconds for 40 cycles.

Allele-specific oligonucleotide PCR

Three microliters of the PCR product prepared as described above was applied to a Hybond N+ membrane (Amersham Lifesciences, Inc., Arlington Heights, Ill.) using a Beckman Biomek Robot. The membranes were air dried and treated with denaturing solution (0.5N NaOH) for 15 minutes, followed by renaturation in 2× SSC with 0.4M tris at pH 7.5 for 10 minutes.

An allele-specific oligonucleotide probe was used to detect the $Arg^{241}$ allele (5'TCCCTGGACAGGCTGTTCC3') (SEQ ID NO: 9). Oligonucleotides were end-labeled with $[\gamma-^{32}P]ATP$ using T4 polynucleotide kinase, and the membranes prehybridized in 10% polyethylene glycol, 7% SDS, 1% bovine serum albumin, 250 mM NaCl, and 250 mM sodium phosphate at 65° C. Hybridization was performed with $2-3\times10^6$ cpm/10 ml of labeled allele-specific oligonucleotide probe (SEQ ID NO: 9) using 20-fold higher concentration of nonradioactive allele-specific oligonucleotide for the alternative allele ($Gly^{241}$). Hybridization was performed at 65° C. for 30 minutes followed by continued hybridization at 37° C. The membranes were washed with 5× SSC at room temperature, followed by 2× SSC at 45° C. for 30 minutes. Results were analyzed by autoradiography.

Although the invention has been described with reference to the examples above, it should be understood that various modifications can be made without departing from the spirit of the invention. Accordingly, the invention is limited only by the following claims.

We claim:

1. A method of diagnosing a clinical subtype of Crohn's disease (CD), comprising determining whether perinuclear anti-neutrophil antibody (pANCA) is present in a patient with CD, wherein determining whether pANCA is present comprises non-histological means, and wherein the presence of pANCA indicates a clinical subtype of CD with features of ulcerative colitis (UC).

2. The method of claim 1, further comprising:

(a) obtaining a serum sample from the patient with CD;

(b) determining by non-histological means whether anti-neutrophil cytoplasmic antibody (ANCA) is detectable in patient sera diluted at least about 100-fold; and (c) assaying for the presence or absence of a pANCA staining pattern, wherein detection of ANCA in patient sera diluted at least about 100-fold and the presence of a pANCA staining pattern indicate the presence of pANCA.

3. The method of claim 1, wherein determining the presence of pANCA comprises:

(a) obtaining a serum sample from the patient with CD;

(b) contacting the serum sample diluted at least about 100-fold with antigen specific for ANCA under conditions suitable to form a first complex of antigen and ANCA;

(c) detecting by non-histological means the presence or absence of said first complex;

(d) contacting an appropriate dilution of the serum sample with antigen specific for ANCA under conditions suitable to form a second complex of antigen specific for ANCA and ANCA; and (e) assaying for the presence or absence of a pANCA staining pattern by detecting the presence or absence of said second complex, wherein the presence of said first complex and the presence of a pANCA staining pattern indicate the presence of pANCA.

4. The method of claim 3, wherein said antigen specific for ANCA in step (d) is neutrophil.

5. The method of claim 3, wherein the serum sample in step (b) is diluted 100-fold.

6. The method of claim 3, wherein the presence or absence of said first complex is detected in an immunoassay.

7. The method of claim 6, wherein said immunoassay is an enzyme-linked immunosorbent assay.

8. The method of claim 4, wherein said antigen specific for ANCA in step (b) is neutrophil.

* * * * *

UNITED STATES PATENT AND TRADEMARK OFFICE
CERTIFICATE OF CORRECTION

PATENT NO. : 5,874,233
DATED : February 23, 1999
INVENTOR(S) : Targan et al.

It is certified that error appears in the above-identified patent and that said Letters Patent is hereby corrected as shown below:

Column 9,
Line 17, please delete "CANCA" and replace with -- cANCA --.
Line 43, please delete "ANCE" and replace with -- ANCA --.

Column 22,
Line 13, please delete "subtypes of" and replace with -- subtypes --.

Signed and Sealed this

Twelfth Day of March, 2002

Attest:

JAMES E. ROGAN
Attesting Officer   Director of the United States Patent and Trademark Office

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 1599 base pairs
( B ) TYPE: nucleic acid
( C ) STRANDEDNESS: single
( D ) TOPOLOGY: linear ( x i ) SEQUENCE DESCRIPTION: SEQ ID NO:1:

```
ATGGCTCCCA  GCAGCCCCG   GCCCGCGCTG  CCCGCACTCC  TGGTCCTGCT  CGGGGCTCTG     60

TTCCCAGGAC  CTGGCAATGC  CCAGACATCT  GTGTCCCCCT  CAAAAGTCAT  CCTGCCCCGG    120

GGAGGCTCCG  TGCTGGTGAC  ATGCAGCACC  TCCTGTGACC  AGCCCAAGTT  GTTGGGCATA    180

GAGACCCCGT  TGCCTAAAAA  GGAGTTGCTC  CTGCCTGGGA  ACAACCGGAA  GGTGTATGAA    240

CTGAGCAATG  TGCAAGAAGA  TAGCCAACCA  ATGTGCTATT  CAAACTGCCC  TGATGGGCAG    300

TCAACAGCTA  AAACCTTCCT  CACCGTGTAC  TGGACTCCAG  AACGGGTGGA  ACTGGCACCC    360

CTCCCCTCTT  GGCAGCCAGT  GGGCAAGAAC  CTTACCCTAC  GCTGCCAGGT  GGAGGGTGGG    420

GCACCCCGGG  CCAACCTCAC  CGTGGTGCTG  CTCCGTGGGG  AGAAGGAGCT  GAAACGGGAG    480

CCAGCTGTGG  GGGAGCCCGC  TGAGGTCACG  ACCACGGTGC  TGGTGAGGAG  AGATCACCAT    540

GGAGCCAATT  TCTCGTGCCG  CACTGAACTG  GACCTGCGGC  CCCAAGGGCT  GGAGCTGTTT    600

GAGAACACCT  CGGCCCCCTA  CCAGCTCCAG  ACCTTTGTCC  TGCCAGCGAC  TCCCCCACAA    660

CTTGTCAGCC  CCCGGGTCCT  AGAGGTGGAC  ACGCAGGGGA  CCGTGGTCTG  TTCCCTGGAC    720

GGGCTGTTCC  CAGTCTCGGA  GGCCCAGGTC  CACCTGGCAC  TGGGGGACCA  GAGGTTGAAC    780

CCCACAGTCA  CCTATGGCAA  CGACTCCTTC  TCGGCCAAGG  CCTCAGTCAG  TGTGACCGCA    840

GAGGACGAGG  GCACCCAGCG  GCTGACGTGT  GCAGTAATAC  TGGGGAACCA  GAGCCAGGAG    900

ACACTGCAGA  CAGTGACCAT  CTACAGCTTT  CCGGCGCCCA  ACGTGATTCT  GACGAAGCCA    960

GAGGTCTCAG  AAGGGACCGA  GGTGACAGTG  AAGTGTGAGG  CCCACCCTAG  AGCCAAGGTG   1020

ACGCTGAATG  GGGTTCCAGC  CCAGCCACTG  GGCCCGAGGG  CCCAGCTCCT  GCTGAAGGCC   1080

ACCCCAGAGG  ACAACGGGCG  CAGCTTCTCC  TGCTCTGCAA  CCCTGGAGGT  GGCCGGCCAG   1140

CTTATACACA  AGAACCAGAC  CCGGGAGCTT  CGTGTCCTGT  ATGGCCCCCG  ACTGGACGAG   1200

AGGGATTGTC  CGGGAAACTG  GACGTGGCCA  GAAAATTCCC  AGCAGACTCC  AATGTGCCAG   1260
```

```
GCTTGGGGGA  ACCCATTGCC  CGAGCTCAAG  TGTCTAAAGG  ATGGCACTTT  CCCACTGCCC    1320

ATCGGGGAAT  CAGTGACTGT  CACTCGAGAT  CTTGAGGGCA  CCTACCTCTG  TCGGGCCAGG    1380

AGCACTCAAG  GGGAGGTCAC  CCGCGAGGTG  ACCGTGAATG  TGCTCTCCCC  CCGGTATGAG    1440

ATTGTCATCA  TCACTGTGGT  AGCAGCCGCA  GTCATAATGG  GCACTGCAGG  CCTCAGCACG    1500

TACCTCTATA  ACCGCCAGCG  GAAGATCAAG  AAATACAGAC  TACAACAGGC  CCAAAAAGGG    1560

ACCCCCATGA  AACCGAACAC  ACAAGCCACG  CCTCCCTGA                             1599
```

( 2 ) INFORMATION FOR SEQ ID NO:2:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CTGCACG                                                                   7

( 2 ) INFORMATION FOR SEQ ID NO:3:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TGCACGG                                                                   7

( 2 ) INFORMATION FOR SEQ ID NO:4:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GCACGGG                                                                   7

( 2 ) INFORMATION FOR SEQ ID NO:5:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CACGGGC                                                                   7

( 2 ) INFORMATION FOR SEQ ID NO:6:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

ACGGGCT                                                                   7

( 2 ) INFORMATION FOR SEQ ID NO:7:

(i) SEQUENCE CHARACTERISTICS:
(A) LENGTH: 7 base pairs
(B) TYPE: nucleic acid
(C) STRANDEDNESS: single
(D) TOPOLOGY: linear (xi) SEQUENCE DESCRIPTION: SEQ ID NO:7:

CGGGCTG  7

(2) INFORMATION FOR SEQ ID NO:8:

(i) SEQUENCE CHARACTERISTICS:
(A) LENGTH: 7 base pairs
(B) TYPE: nucleic acid
(C) STRANDEDNESS: single
(D) TOPOLOGY: linear (xi) SEQUENCE DESCRIPTION: SEQ ID NO:8:

GGGCTGT  7

(2) INFORMATION FOR SEQ ID NO:9:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:9:

TCCCTGGACA GGCTGTTCC  19

(2) INFORMATION FOR SEQ ID NO:10:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:10:

GATTGAAGAA GCCAGCAG  18

(2) INFORMATION FOR SEQ ID NO:11:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:11:

GTCGTTGCCA TAGGTGAC  18

(2) INFORMATION FOR SEQ ID NO:12:

(i) SEQUENCE CHARACTERISTICS:
(A) LENGTH: 532 amino acids
(B) TYPE: amino acid
(C) STRANDEDNESS: single
(D) TOPOLOGY: linear (ix) FEATURE:
(A) NAME/KEY: CDS
(B) LOCATION: 1..1599

(xi) SEQUENCE DESCRIPTION: SEQ ID NO:12:

Met Ala Pro Ser Ser Pro Arg Pro Ala Leu Pro Ala Leu Leu Val Leu
 1               5                  10                  15

```
Leu  Gly  Ala  Leu  Phe  Pro  Gly  Pro  Gly  Asn  Ala  Gln  Thr  Ser  Val  Ser
          20                       25                      30

Pro  Ser  Lys  Val  Ile  Leu  Pro  Arg  Gly  Gly  Ser  Val  Leu  Val  Thr  Cys
          35                       40                      45

Ser  Thr  Ser  Cys  Asp  Gln  Pro  Lys  Leu  Leu  Gly  Ile  Glu  Thr  Pro  Leu
     50                       55                      60

Pro  Lys  Lys  Glu  Leu  Leu  Leu  Pro  Gly  Asn  Asn  Arg  Lys  Val  Tyr  Glu
65                       70                       75                       80

Leu  Ser  Asn  Val  Gln  Glu  Asp  Ser  Gln  Pro  Met  Cys  Tyr  Ser  Asn  Cys
                         85                       90                       95

Pro  Asp  Gly  Gln  Ser  Thr  Ala  Lys  Thr  Phe  Leu  Thr  Val  Tyr  Trp  Thr
               100                      105                     110

Pro  Glu  Arg  Val  Glu  Leu  Ala  Pro  Leu  Pro  Ser  Trp  Gln  Pro  Val  Gly
               115                      120                     125

Lys  Asn  Leu  Thr  Leu  Arg  Cys  Gln  Val  Glu  Gly  Gly  Ala  Pro  Arg  Ala
          130                      135                     140

Asn  Leu  Thr  Val  Val  Leu  Leu  Arg  Gly  Glu  Lys  Glu  Leu  Lys  Arg  Glu
145                      150                      155                      160

Pro  Ala  Val  Gly  Glu  Pro  Ala  Glu  Val  Thr  Thr  Thr  Val  Leu  Val  Arg
               165                      170                     175

Arg  Asp  His  His  Gly  Ala  Asn  Phe  Ser  Cys  Arg  Thr  Glu  Leu  Asp  Leu
               180                      185                     190

Arg  Pro  Gln  Gly  Leu  Glu  Leu  Phe  Glu  Asn  Thr  Ser  Ala  Pro  Tyr  Gln
          195                      200                     205

Leu  Gln  Thr  Phe  Val  Leu  Pro  Ala  Thr  Pro  Pro  Gln  Leu  Val  Ser  Pro
     210                      215                     220

Arg  Val  Leu  Glu  Val  Asp  Thr  Gln  Gly  Thr  Val  Val  Cys  Ser  Leu  Asp
225                      230                      235                      240

Gly  Leu  Phe  Pro  Val  Ser  Glu  Ala  Gln  Val  His  Leu  Ala  Leu  Gly  Asp
               245                      250                     255

Gln  Arg  Leu  Asn  Pro  Thr  Val  Thr  Tyr  Gly  Asn  Asp  Ser  Phe  Ser  Ala
          260                      265                     270

Lys  Ala  Ser  Val  Ser  Val  Thr  Ala  Glu  Asp  Glu  Gly  Thr  Gln  Arg  Leu
          275                      280                     285

Thr  Cys  Ala  Val  Ile  Leu  Gly  Asn  Gln  Ser  Gln  Glu  Thr  Leu  Gln  Thr
     290                      295                     300

Val  Thr  Ile  Tyr  Ser  Phe  Pro  Ala  Pro  Asn  Val  Ile  Leu  Thr  Lys  Pro
305                      310                      315                      320

Glu  Val  Ser  Glu  Gly  Thr  Glu  Val  Thr  Val  Lys  Cys  Glu  Ala  His  Pro
               325                      330                     335

Arg  Ala  Lys  Val  Thr  Leu  Asn  Gly  Val  Pro  Ala  Gln  Pro  Leu  Gly  Pro
               340                      345                     350

Arg  Ala  Gln  Leu  Leu  Leu  Lys  Ala  Thr  Pro  Glu  Asp  Asn  Gly  Arg  Ser
          355                      360                     365

Phe  Ser  Cys  Ser  Ala  Thr  Leu  Glu  Val  Ala  Gly  Gln  Leu  Ile  His  Lys
     370                      375                     380

Asn  Gln  Thr  Arg  Glu  Leu  Arg  Val  Leu  Tyr  Gly  Pro  Arg  Leu  Asp  Glu
385                      390                      395                      400

Arg  Asp  Cys  Pro  Gly  Asn  Trp  Thr  Trp  Pro  Glu  Asn  Ser  Gln  Gln  Thr
               405                      410                     415

Pro  Met  Cys  Gln  Ala  Trp  Gly  Asn  Pro  Leu  Pro  Glu  Leu  Lys  Cys  Leu
               420                      425                     430

Lys  Asp  Gly  Thr  Phe  Pro  Leu  Pro  Ile  Gly  Glu  Ser  Val  Thr  Val  Thr
```

|     |     |     |     |     | 435 |     |     |     |     | 440 |     |     |     |     | 445 |     |     |     |     |
| --- | --- | --- | --- | --- | --- | --- | --- | --- | --- | --- | --- | --- | --- | --- | --- | --- | --- | --- | --- |
| Arg | Asp 450 | Leu | Glu | Gly | Thr | Tyr 455 | Leu | Cys | Arg | Ala | Arg 460 | Ser | Thr | Gln | Gly |
| Glu 465 | Val | Thr | Arg | Glu | Val 470 | Thr | Val | Asn | Val | Leu 475 | Ser | Pro | Arg | Tyr | Glu 480 |
| Ile | Val | Ile | Ile | Thr 485 | Val | Val | Ala | Ala | Ala 490 | Val | Ile | Met | Gly | Thr 495 | Ala |
| Gly | Leu | Ser | Thr 500 | Tyr | Leu | Tyr | Asn | Arg 505 | Gln | Arg | Lys | Ile | Lys 510 | Lys | Tyr |
| Arg | Leu | Gln 515 | Gln | Ala | Gln | Lys | Gly 520 | Thr | Pro | Met | Lys | Pro 525 | Asn | Thr | Gln |
| Ala | Thr 530 | Pro | Pro |     |     |     |     |     |     |     |     |     |     |     |     |